US 9,155,573 B2

(12) United States Patent
May et al.

(10) Patent No.: US 9,155,573 B2
(45) Date of Patent: Oct. 13, 2015

(54) SPINAL CORRECTION SYSTEM

(71) Applicant: Warsaw Orthopedic, Inc., Warsaw, IN (US)

(72) Inventors: Jason May, Cordova, TN (US); William Alan Rezach, Atoka, TN (US); Molly Rice, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/659,590

(22) Filed: Oct. 24, 2012

(65) Prior Publication Data
US 2014/0114354 A1   Apr. 24, 2014

(51) Int. Cl.
*A61B 17/88* (2006.01)
*A61B 17/70* (2006.01)

(52) U.S. Cl.
CPC ................... *A61B 17/7077* (2013.01)

(58) Field of Classification Search
CPC .......... A61B 17/7059; A61B 17/7014; A61B 17/7043; A61B 17/7074; A61B 17/88; A61B 17/7019; A61B 17/7049; A61B 17/705; A61B 17/7052
USPC ................... 606/246, 248, 249, 279
See application file for complete search history.

(56) References Cited

U.S. PATENT DOCUMENTS

| 5,389,222 A * | 2/1995 | Shahinpoor ................... 310/309 |
| 6,033,412 A * | 3/2000 | Losken et al. ............... 606/105 |
| 6,190,414 B1 * | 2/2001 | Young et al. ............... 623/17.15 |
| 8,097,021 B1 * | 1/2012 | Kornel .......................... 606/248 |
| 2006/0058792 A1 * | 3/2006 | Hynes ............................. 606/61 |
| 2007/0118129 A1 * | 5/2007 | Fraser et al. .................... 606/71 |
| 2007/0162009 A1 * | 7/2007 | Chao et al. ..................... 606/61 |
| 2008/0140207 A1 * | 6/2008 | Olmos et al. ............... 623/17.16 |
| 2010/0298885 A1 * | 11/2010 | Tribus .......................... 606/279 |
| 2011/0054528 A1 * | 3/2011 | Michelson .................... 606/246 |
| 2012/0184995 A1 * | 7/2012 | Miller .......................... 606/264 |
| 2013/0211453 A1 * | 8/2013 | Lenke et al. ................. 606/250 |

* cited by examiner

*Primary Examiner* — Eduardo C Robert
*Assistant Examiner* — Tessa Matthews
(74) *Attorney, Agent, or Firm* — Sorell Lenna & Schmidt LLP

(57) ABSTRACT

A spinal correction system comprises a first member defining a longitudinal axis and including an inner surface that defines a first cavity and a second cavity. A second member defines a longitudinal axis and includes an inner surface that defines a first cavity and a second cavity. The members are connected along a first axis disposed in substantially parallel relation to the longitudinal axes. At least one first implant support is configured for disposal within the first cavities. At least one second implant support is configured for disposal within the second cavities. The members are rotatable about the first axis to space apart the members such that the inner surfaces forcibly engage the supports in releasable fixation. Methods of use are disclosed.

20 Claims, 19 Drawing Sheets

SPINAL CORRECTION SYSTEM

TECHNICAL FIELD

The present disclosure generally relates to medical devices for the treatment of musculoskeletal disorders, and more particularly to a surgical system for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments may employ implants that are manipulated for engagement with vertebrae to position and align one or more vertebrae. This disclosure describes an improvement over these prior art technologies.

SUMMARY

Accordingly, a surgical system for correction of a spine disorder is provided. In one particular embodiment, in accordance with the principles of the present disclosure, a spinal correction system comprises a first member defining a longitudinal axis and including an inner surface that defines a first cavity and a second cavity. A second member defines a longitudinal axis and includes an inner surface that defines a first cavity and a second cavity. The members are connected along a first axis disposed in substantially parallel relation to the longitudinal axes. At least one first implant support is configured for disposal within the first cavities. At least one second implant support is configured for disposal within the second cavities. The members are rotatable about the first axis to space apart the members such that the inner surfaces forcibly engage the supports in releasable fixation.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
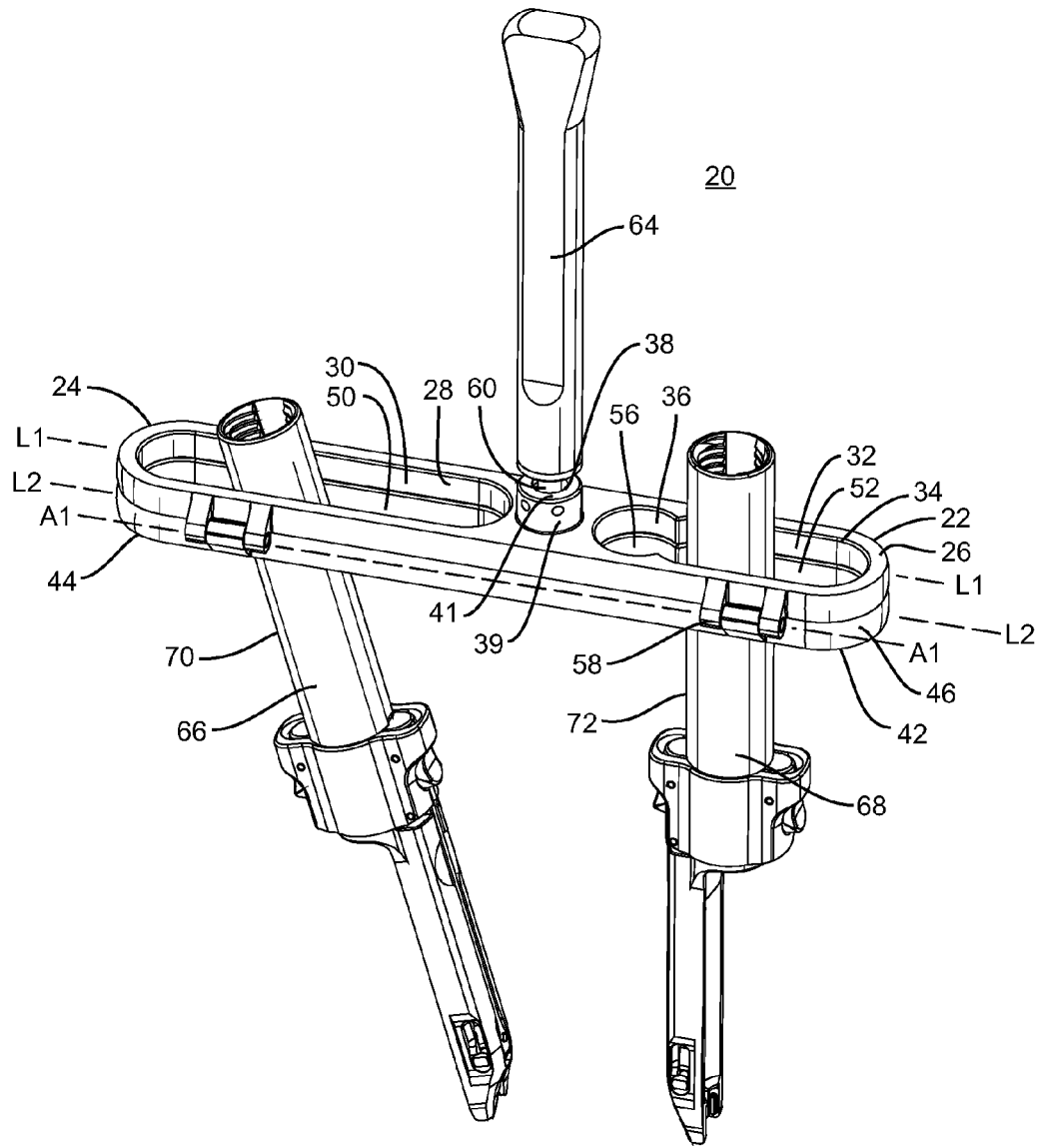
FIG. 1 is a perspective view of one embodiment of a system in accordance with the principles of the present disclosure.

The exemplary embodiments of the spinal correction system and related methods of use disclosed are discussed in terms of medical devices for the treatment of musculoskeletal disorders and more particularly, in terms of a spinal correction system that facilitates implant delivery and treatment of a spine. It is envisioned that the spinal correction system can include extenders, reducers and translators, which can be used to introduce a vertebral construct such as a rod to a bone fastener, such as a bone anchor or bone screw. For example, an extender can include bone anchor attachment features on one or both sides of the instrument. It is contemplated that the system may be used with a reducer assembly to introduce a rod into a bone fastener.

In one embodiment, the system is employed with a method for deformity correction, for example, treatment of scoliosis. It is contemplated that the system is employed for axial derotation of vertebral bodies to improve chest wall volume and pulmonary function. In one embodiment, the system includes pedicle screws placed in the vertebral bodies that provide anchors for spinal manipulation. In one embodiment, the system includes implant supports, such as, for example, extenders attached to the pedicle screws that are configured as derotation levers and are linked together to distribute derotation forces applied to components of the system. In one embodiment, the system is configured for linking two extenders across a single vertebral body in a segmental configuration. In one embodiment, the system is configured for linking extenders across a plurality of vertebral bodies in a global or en bloc configuration.

In one embodiment, the system includes a clamping mechanism that includes plates with features to engage an implant support. In one embodiment, the clamping mechanism includes arms hinged together and pivot normal to an axis of an implant support such that the clamping mechanism actuates along the axis. In one embodiment, the clamping mechanism is movable between unlocked and locked positions. For example, in the unlocked position, the clamping mechanism is free to travel along the axis of the implant support. For example, in the locked position, the clamping mechanism is secured with frictional force on the implant support to prevent movement along the axis of the implant support. In one embodiment, the clamping mechanism includes an actuator, which can include, for example, a spring or a screw jack or other manual actuation. This configuration can eliminate locking steps during surgery. In one embodiment, the system facilitates translation of the implant supports in a sagittal plane during derotation. This configuration can improve kyphosis or reduce flat back.

In one embodiment, the system includes a segmental link. The segmental link includes plates connected with spaced apart hinges. The plates define slots configured for disposal of concave and convex implant supports. In one embodiment, the link includes a tightening/derotation handle. In one embodiment, the slot geometry includes an opening configured for accommodation of a multi-axial screw (MAS). In one embodiment, the plates are movable between an open position and a clamped position.

In one embodiment, the system includes a frame connected with one or a plurality of links, which are configured for disposal with a plurality of vertebral levels. In one embodiment, the link includes one or a plurality of actuators, such as, for example, a tightening handle. In one embodiment, the link includes one or a plurality of derotation handles. In one embodiment, the frame has an adjustment slot with positioning notches. In one embodiment, the frame has a concave hinge that facilitates pivoting and relative movements of links connected to the frame. In one embodiment, the link includes slots configured for disposal of concave and convex extenders. In one embodiment, the link includes slots disposed in a cephalad/caudal orientation, which allows for sagittal plane adjustment.

It is envisioned that the spinal correction system may include instruments that are connected or attached to an extender(s) such as, for example, a lateral translation handle or derotation instruments. In one embodiment, one or all of the components of the surgical system are disposable, peel-pack, pre-packed sterile devices used with a spinal correction system. One or all of the components of the spinal correction system may be reusable. The spinal correction system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-5, there is illustrated components of a surgical system, such as, for example, a spinal correction system 20 in accordance with the principles of the present disclosure.

The components of spinal correction system 20 can be fabricated from biologically acceptable materials suitable for medical applications, including metals, synthetic polymers, ceramics and bone material and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglyclolide, polytyrosine carbonate, polycaroplaetohe and their combinations. Various components of spinal correction system 20 may have material composites, including the above materials, to achieve various desired characteristics such as strength, rigidity, elasticity, compliance, biomechanical performance, durability and radiolucency or imaging preference. The components of spinal correction system 20, individually or collectively, may also be fabricated from a heterogeneous material such as a combination of two or more of the above-described materials. The components of spinal correction system 20 may be monolithically formed, integrally connected or include fastening elements and/or instruments, as described herein.

Spinal correction system 20 is employed, for example, with an open or mini-open, minimal access and/or minimally invasive including percutaneous surgical technique for engagement with an implant, such as, for example, a bone fastener for a correction treatment at a surgical site within a body of a patient, for example, a section of a spine to treat various spine pathologies, such as, for example, adolescent idiopathic scoliosis and Scheuermann's kyphosis. In one embodiment, the components of spinal correction system 20 are configured to deliver and introduce an implant, such as, for example, a vertebral construct such as a rod to a bone fastener.

Spinal correction system 20 includes a first member, such as, for example, a plate 22 defining a longitudinal axis L1.

Plate 22 extends between a first end 24 and a second end 26. Plate 22 defines an inner surface 28. It is contemplated that inner surface 28 may have alternate surface configurations, such as, for example, rough, arcuate, undulating, mesh, porous, semi-porous, dimpled and/or textured according to the requirements of a particular application. Inner surface 28 defines a first cavity, such as, for example, a first elongated slot 30 and a second cavity, such as, for example, a second elongated slot 32.

Figure 2:
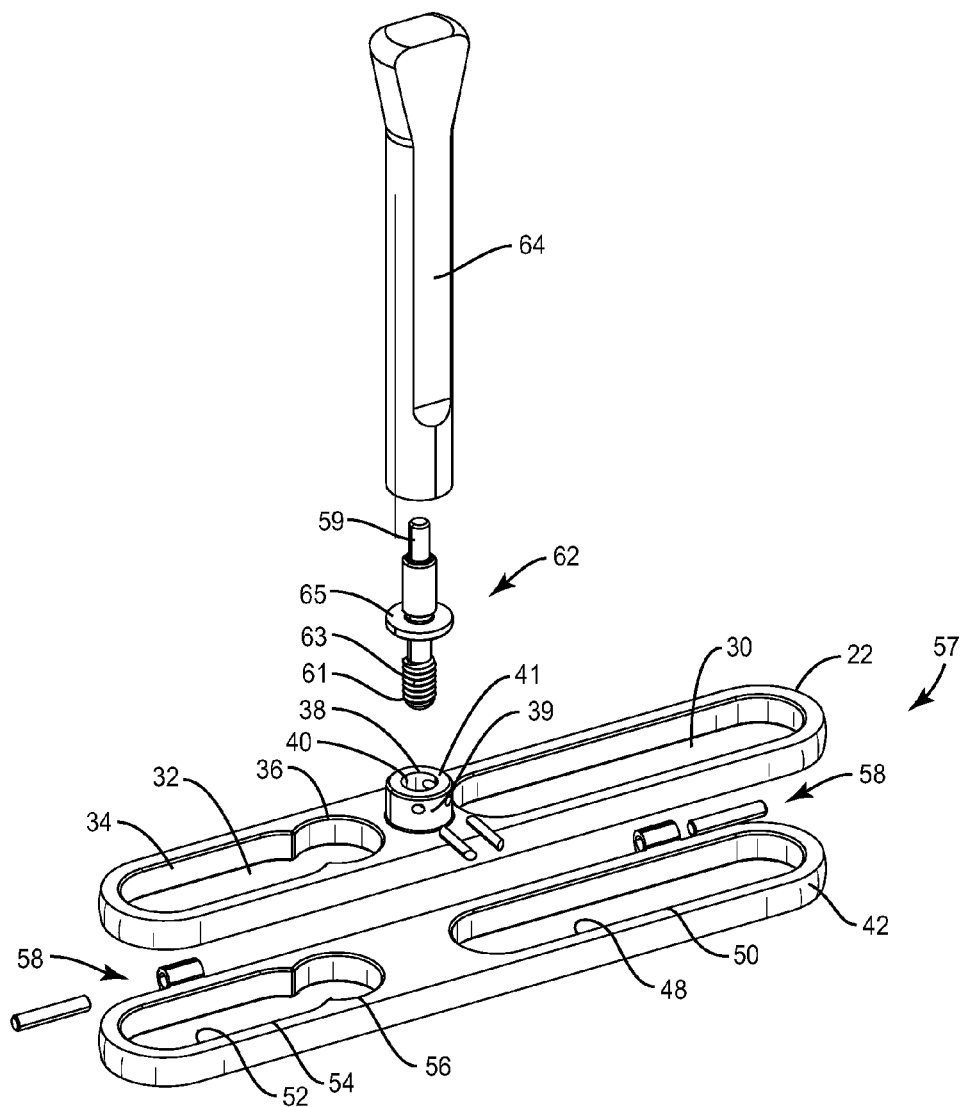
FIG. 2 is a perspective view of components of the system shown in FIG. 1 with parts separated.
Figure 3:
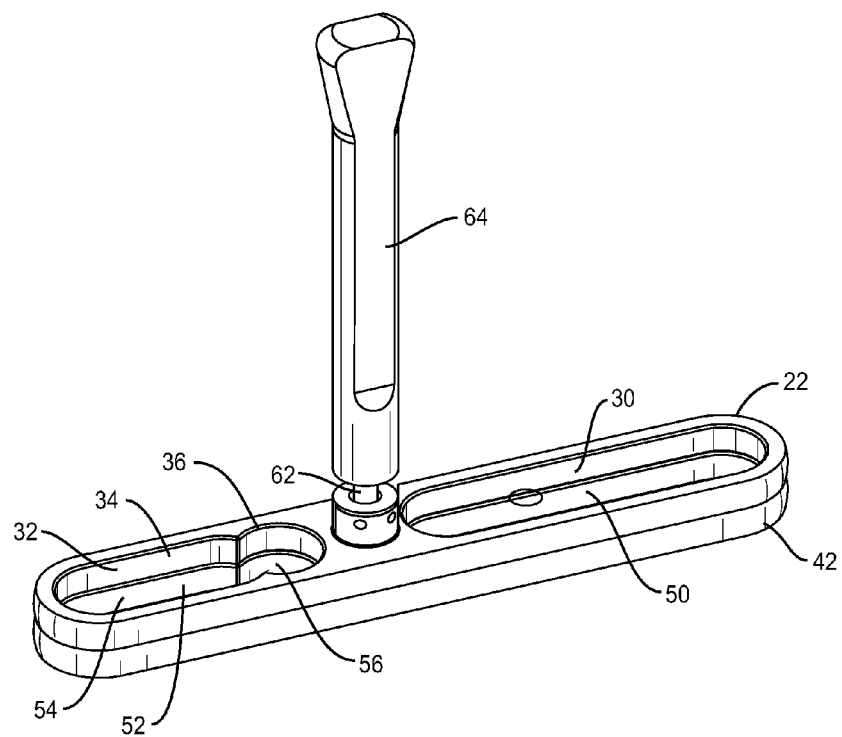
FIG. 3 is a perspective view of components of the system shown in FIG. 1.

Slots 30, 32 are each configured to receive a surgical instrument, such as, for example, an implant support. Slots 30, 32 are spaced apart along axis L1 and disposed in a transverse plane T (FIG. 6) relative to, for example, vertebrae of a body. In one embodiment, as shown in FIG. 2, one of slots 30, 32, such as, for example, slot 32 includes an elongated portion 34 and an arcuate portion 36. Portion 34 is configured for disposal of the implant support along plane T and arcuate portion 36 is configured to prevent rotation of the implant support in plane T and translation of the implant support along axis L1, as discussed herein. It is envisioned that slots 30, 32 may be variously configured and dimensioned, such as, for example, round, oval, oblong, square, rectangular, polygonal, irregular, uniform, non-uniform, offset, staggered, tapered, consistent or variable, depending on the requirements of a particular application.

Plate 22 includes a surface 40 that defines a third cavity, such as, for example an opening 38. Inner surface 40 is threaded and opening 38 is configured for disposal of an actuator, discussed herein. It is contemplated that surface 40 may have alternate surface configurations, such as, for example, rough, arcuate, undulating, mesh, porous, semi-porous, dimpled and/or textured according to the requirements of a particular application. Plate 22 includes a raised portion 39 having a face 41 configured for engagement with an actuator, as discussed herein.

Spinal correction system 20 includes a second member, such as, for example, a plate 42 defining a longitudinal axis L2. Plate 42 extends between a first end 44 and a second end 46. Plate 42 defines an inner surface 48. It is contemplated that inner surface 48 may have alternate surface configurations, such as, for example, rough, arcuate, undulating, mesh, porous, semi-porous, dimpled and/or textured according to the requirements of a particular application. Inner surface 48 defines a first cavity, such as, for example, a first elongated slot 50 and a second cavity, such as, for example, a second elongated slot 52.

Slots 50, 52 are each configured to receive a surgical instrument, such as, for example, an implant support. Slots 50, 52 are spaced apart along axis L2 and disposed in plane T such that at least a portion of slots 30, 50 and slots 32, 52 are substantially aligned. In one embodiment, as shown in FIG. 2, one of slots 50, 52, such as, for example, slot 52 includes an elongated portion 54 and an arcuate portion 56. Portion 54 is configured for disposal of the implant support along plane T and arcuate portion 56 is configured to prevent rotation of the implant support in plane T and translation of the implant support along axis L2, as discussed herein. It is contemplated that only one or both of plates 22, 42 may include an arcuate portion, as described herein. In one embodiment, portions 34, 54 support an extender connected with a mono-axial bone screw and portions 36, 56 support an extender connected with a MAS. It is envisioned that slots 50, 52 may be variously configured and dimensioned, such as, for example, round, oval, oblong, square, rectangular, polygonal, irregular, uniform, non-uniform, offset, staggered, tapered, consistent or variable, depending on the requirements of a particular application.

Plates 22, 42 are configured to form an apparatus, such as, for example, a segmental link 57. Plate 22 is connected to plate 42 along a first axis A1. Axis A1 is disposed in substantially parallel relation to longitudinal axes L1 and L2. Plates 22, 42 are rotatable about axis A1 between a non-locking configuration and a locking configuration to space apart plates 22, 42 such that inner surfaces 28, 48 forcibly engage the implant supports disposed therein in releasable fixation. In one embodiment, as shown in FIGS. 1 and 2, plates 22, 42 are connected via a first hinge 58 that is spaced apart from a second hinge 58 and extending along axis A1. Hinges 58 facilitate relative rotation of plates 22, 42.

System 20 includes an actuator, such as, for example, a screw jack 60 engageable with plates 22, 42. Screw jack 60 actuates link 57 to drive apart plates 22, 42 and rotate plates 22, 42 about axis A1. Screw jack 60 includes an elongated post 62 having a proximal end 59 and a distal end 61. Distal end 61 includes a threaded portion 63 configured to threadably engage surface 40. A flange 65 extends circumferentially about post 62 and is disposed proximal to threaded portion 63. Flange 65 is configured to engage face 41.

Figure 5:
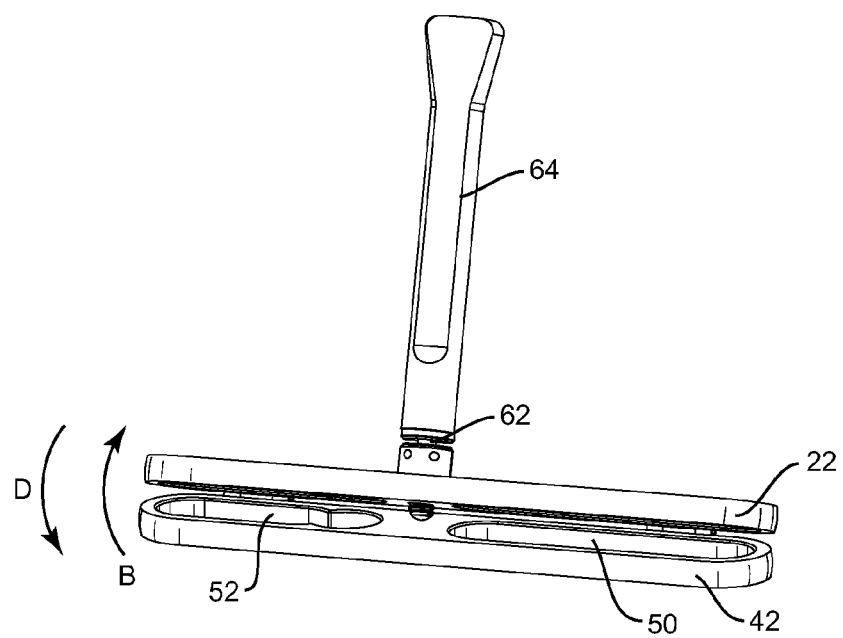
FIG. 5 is a perspective view of the components shown in FIG. 3.

A handle 64 is mounted with proximal end 59 to facilitate actuation of screw jack 60. Handle 64 is configured for rotation, for example, in a clockwise and counterclockwise direction, to translate threaded portion 63 relative to plate 22 to engage plate 42 to drive apart plates 22, 42. Handle 64 is rotated in a clockwise direction and portion 63 engages plate 42 such that plate 22 is driven apart from plate 42 about axis A1 to a locking configuration, as shown in FIG. 5. In the locking configuration, inner surfaces 28, 48 forcibly engage the implant supports disposed therein in releasable fixation.

Figure 4:
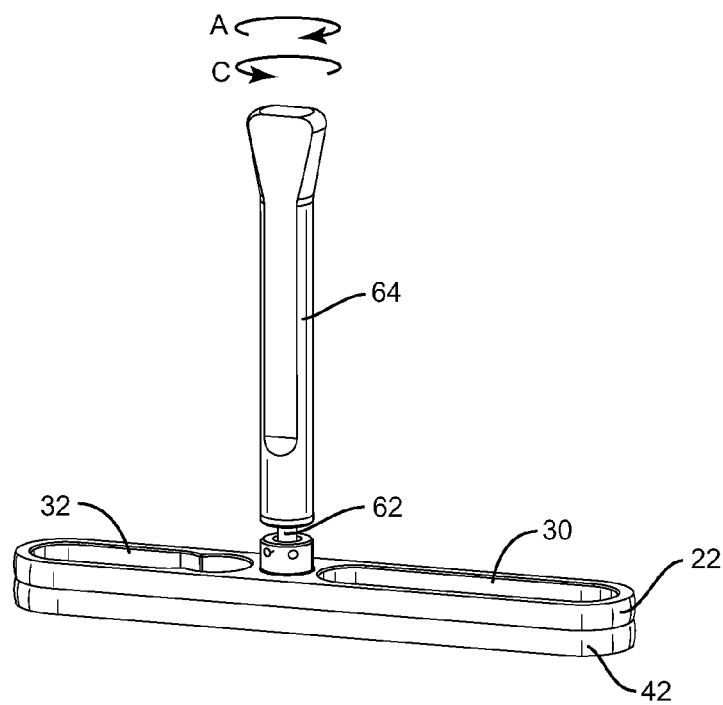
FIG. 4 is a perspective view of the components shown in FIG. 3.

Handle 64 is rotated in a counter clockwise direction and portion 63 translates out of engagement with plate 42 such that plate 22 is rotated into close proximity and/or contacting relation with plate 42 to a non-locking configuration, as shown in FIG. 4. In the non-locking configuration, the implant supports are released from fixation with plates 28, 48 and freely slidable in the slots, as described. In one embodiment, handle 64 is configured for manipulation and resultant application of one or a plurality of forces and/or moments for application to a body to create for example, a derotation force for a spinal treatment. It is envisioned that handle 64 may be employed to displace, pull, twist or align vertebrae, according to the requirements of a particular application.

Handle 64 is rotated to space apart plates 22, 42 in a range corresponding to the translation of screw jack 60 relative to plate 22. Screw jack 60 is configured to engage threaded surface 40 of plate 22 such that screw jack 62 translates along and through opening 38 to engage plate 42. In one embodiment, the range of translation of screw jack 60 relative to plate 22 is between engagement of threaded portion 63 and translation up to engagement of flange 65 and face 41. Engagement of flange 65 and face 41 prevents plates 22, 42 from further rotation and separation. In one embodiment, the actuator includes a spring mechanism (not shown) utilized to space apart and/or draw together plates 22, 42.

In operation, the components of system 20 are disposable between a first, non-locking configuration, as shown in FIG. 4 and a second, locking configuration, as shown in FIG. 5. In the non-locking configuration, no appreciable force is applied to the implant supports. The implant supports are freely slidable for transverse translation within slots 30, 50 and/or slots 32, 52. In one embodiment, an implant support can be selectively translated along slots 30, 50 and/or slots 32, 52 and positioned at a selected orientation. In one embodiment, an implant support can be disposed along portions 34, 54, for example, with a mono-axial or fixed axis screw and/or can be disposed with portions 36, 56, for example, with a MAS such that rotation of the implant support is prevented and translation of the implant support along axes L1, L2 is prevented.

Handle 64 is rotated in a clockwise direction, in the direction shown by arrow A in FIG. 4, and portion 63 engages plate 42, for example translating in a distal direction relative to plate 22, such that plate 22 is rotated relative to plate 42 about axis A1, in the direction shown by arrow B in FIG. 5, and driven apart from plate 42 to a locking configuration, as shown in FIG. 5. In the locking configuration, inner surfaces 28, 48 forcibly engage the implant supports disposed therein in releasable fixation to dispose the implant supports in the selected position and/or orientation. The pivoting of plate 22 relative to plate 42 drives inner surfaces 28, 48 into fixed engagement with the implant supports. In the locking configuration, plates 22, 42 are locked with the implant supports.

The components of system 20 can be released from the locking configuration and pivoted to the non-locking configuration, as shown in FIG. 4. Handle 64 is rotated counter clockwise, in the direction shown by arrow C in FIG. 4, and portion 63 translates out of engagement with plate 42, for example, translating in a proximal direction relative to plate 22, such that plate 22 is rotated relative to plate 42 about axis A1, in the direction shown by arrow D in FIG. 5, into close proximity and/or contacting relation with plate 42 to a non-locking configuration. In the non-locking configuration, the implant supports are released from fixation with plates 22, 42 and freely slidable in the slots, as described.

Figure 6:
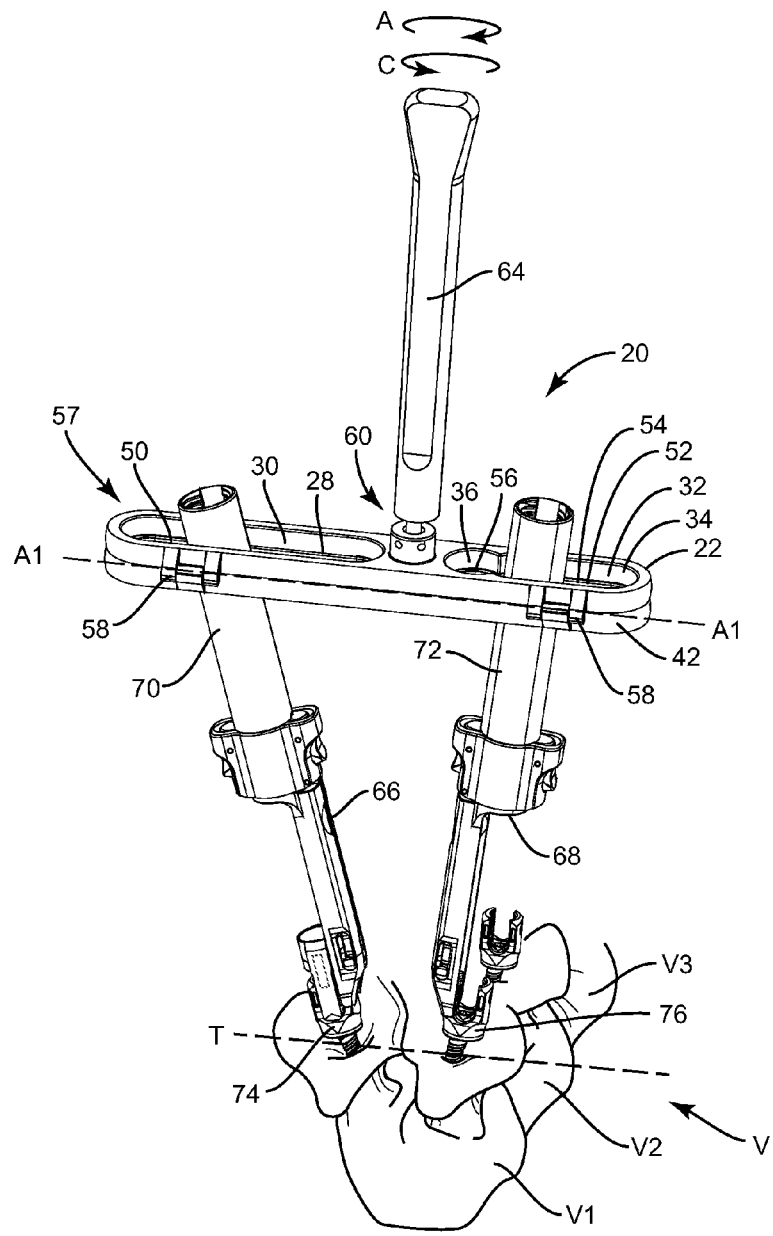
FIG. 6 is a perspective view of one embodiment of a system in accordance with the principles of the present disclosure disposed with vertebrae.

In one embodiment, system 20 includes a first implant support, such as, for example a first extender 66 and a second implant support, such as, for example a second extender 68, as shown in FIG. 6. Extender 66 includes an outer surface 70 configured for disposal with slots 30, 50 and engagement with surfaces 28, 48. In one embodiment, extender 66 is configured for connection with a bone fastener disposed with a concave portion of a spine. Extender 68 includes an outer surface 72 configured for disposal with slots 32, 52 and engagement with surfaces 28, 48. In one embodiment, extender 68 is configured for connection with a bone fastener disposed with a convex portion of a spine. It is contemplated that system 20 may include one or a plurality of extenders disposed with each of the slots.

In assembly, operation and use, spinal correction system 20, similar to the system described above, is employed with a surgical procedure, such as, for example, a correction treatment to treat adolescent idiopathic scoliosis and/or Scheuermann's kyphosis of a spine. It is contemplated that one or all of the components of spinal correction system 20 can be delivered or utilized as a pre-assembled device or can be assembled in situ.

For example, spinal correction system 20 can be employed with a surgical correction treatment of an applicable condition or injury of an affected section of a spinal column and adjacent areas within a body, such as, for example, vertebral levels V1, V2, V3 of vertebrae V, as shown in FIG. 6. It is envisioned that spinal correction system 20 may be employed with one or a plurality of vertebrae.

In use, to treat vertebrae V, a medical practitioner obtains access to a surgical site including vertebrae V in any appropriate manner, such as through incision and retraction of tissues. It is envisioned that spinal correction system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V1, V2 and V3, as well as for aspiration and irrigation of a surgical region according to the requirements of a particular surgical application.

Pilot holes (not shown) are made bilaterally in selected levels of vertebrae V, for example, vertebrae V1, V2 and V3 for receiving bone fasteners 74, 76. Extenders 66, 68 are oriented for manipulation, alignment and capture of bone fasteners 74, 76. Extender 66 is configured for disposal with a concave portion of a selected vertebra of vertebrae V and extender 68 is configured for disposal with a convex portion of a selected vertebra of vertebrae V.

Extenders 66, 68 are attached with vertebra V1 via bone fasteners 74, 76, such that the components of system 20 are disposed in the non-locking configuration, as described. Extenders 66, 68 are freely slidable for transverse translation within slots 30, 50 and/or slots 32, 52 such that extenders 66, 68 support can be selectively translated along slots 30, 50 and/or slots 32, 52 and positioned at a selected orientation.

Handle 64 is rotated in a clockwise direction, in the direction shown by arrow A in FIG. 4, such that plate 22 is rotated relative to plate 42 about axis A1, in the direction shown by arrow B in FIG. 5, and driven apart from plate 42 to the locking configuration, as shown in FIG. 5 and described above. Inner surfaces 28, 48 forcibly engage extenders 66, 68 in releasable fixation to fixedly dispose extenders 66, 68 in the selected position and/or orientation. Plates 22, 42 are locked with extenders 66, 68.

Force is applied to handle 64, for example, via manipulation of a practitioner during a surgical treatment, to displace, pull, twist or align vertebrae, according to the requirements of a particular application. Upon completion of practitioner manipulation, the components of system 20 can be released from the locking configuration and pivoted to the non-locking configuration, as described.

Figure 7:
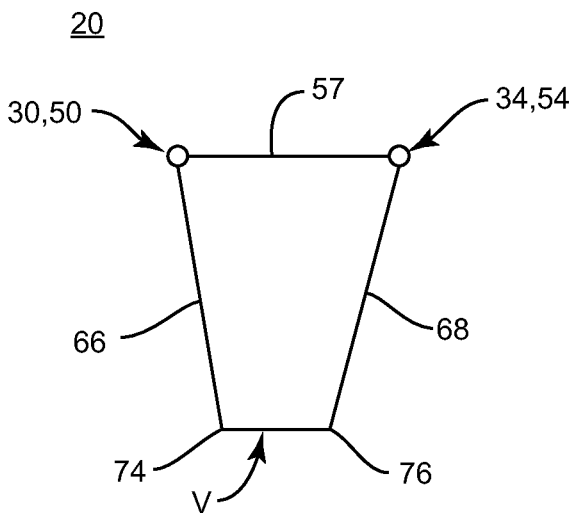
FIG. 7 is a schematic representation of one embodiment of a system in accordance with the principles of the present disclosure disposed with vertebrae.

In one embodiment, as shown in FIG. 7, link 57 is configured with a locking linkage of system 20 employed with fixed axial screws 74, 76. The linkage of system 20 includes a first joint, such as, for example, extender 66 disposed with slots 30, 50 described above, and a second joint, such as, for example, extender 68 disposed with portions 34, 54 described above. The first joint and the second joint facilitate fixing link 57 in the locking configuration, as described herein.

Figure 8:
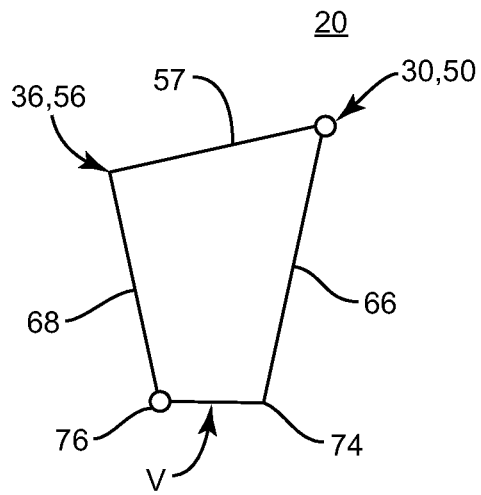
FIG. 8 is a schematic representation of one embodiment of a system in accordance with the principles of the present disclosure disposed with vertebrae.

In one embodiment, as shown in FIG. 8, link 57 is configured with a locking linkage of system 20 employed with a fixed axial screw 74 and a MAS 76. The linkage of system 20 includes a first joint, such as, for example, extender 66 disposed with slots 30, 50 described above, and a second joint, such as, for example, the spherical joint of the MAS crown and the MAS bone screw of MAS 76. Extender 68 is disposed with portions 36, 56 described above, such that link 57 is disposed perpendicular to extender 68 and the rotation of link 57 with extender 68 is fixed. The first joint and the second joint facilitate fixing link 57 in the locking configuration, as described herein.

It is envisioned that system 20 may include and/or be employed with various bone fasteners, including those described herein and for example, anchors, expanding screws, wedges, clips, friction fittings, compressive fittings, expanding rivets, staples, nails, fixation plates and/or posts. It is envisioned that the use of microsurgical and image guided technologies may be employed to access, view and repair spinal deterioration or damage, with the aid of spinal correction system 20. Upon completion of the procedure, the non-implanted components, surgical instruments and assemblies are removed and the incision is closed.

It is contemplated that the components of spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of spinal correction system 20 and method of use may be used to prevent or minimize curve progression in individuals of various ages.

Figure 9:
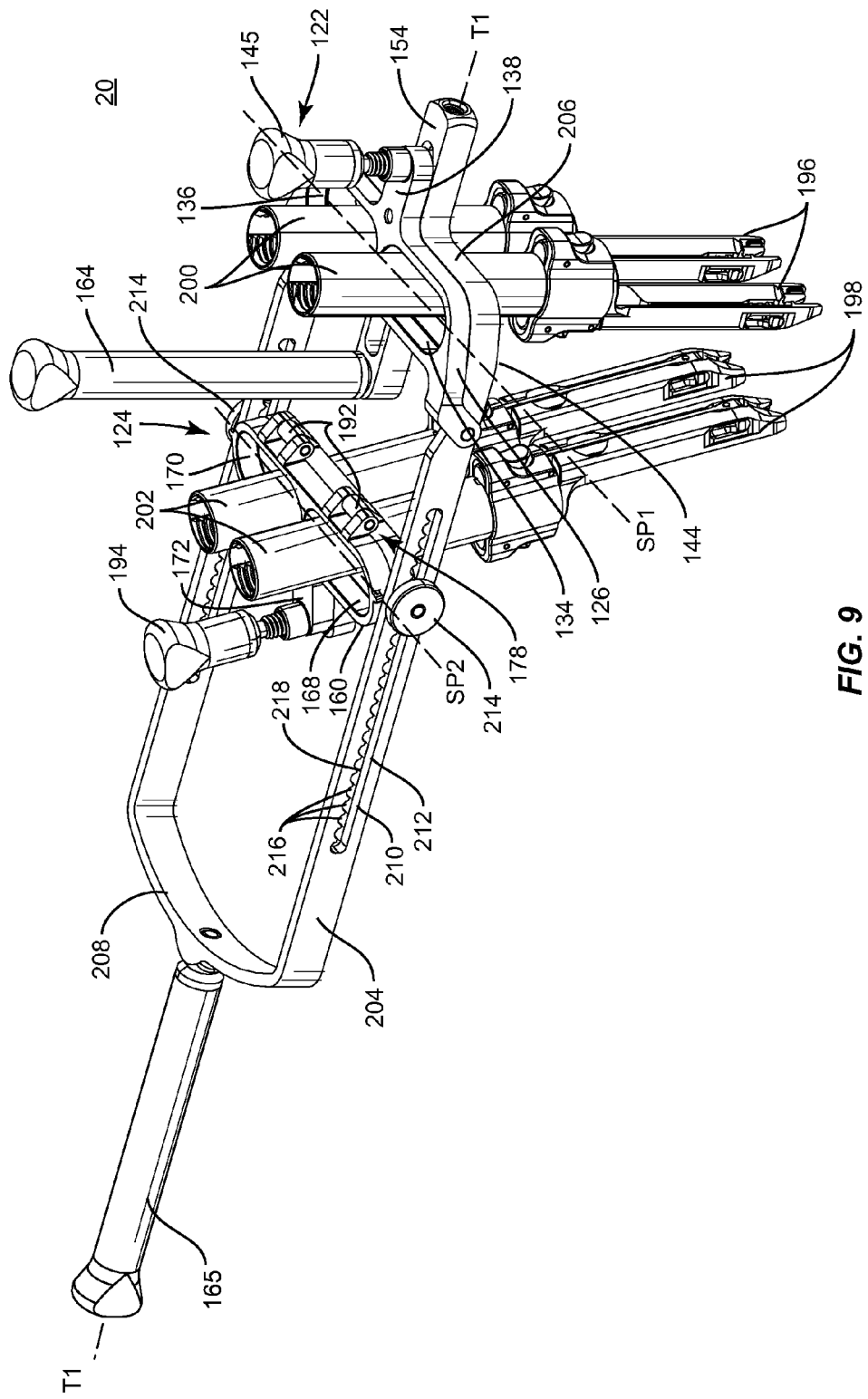
FIG. 9 is a perspective view of one embodiment of a system in accordance with the principles of the present disclosure.
Figure 10:
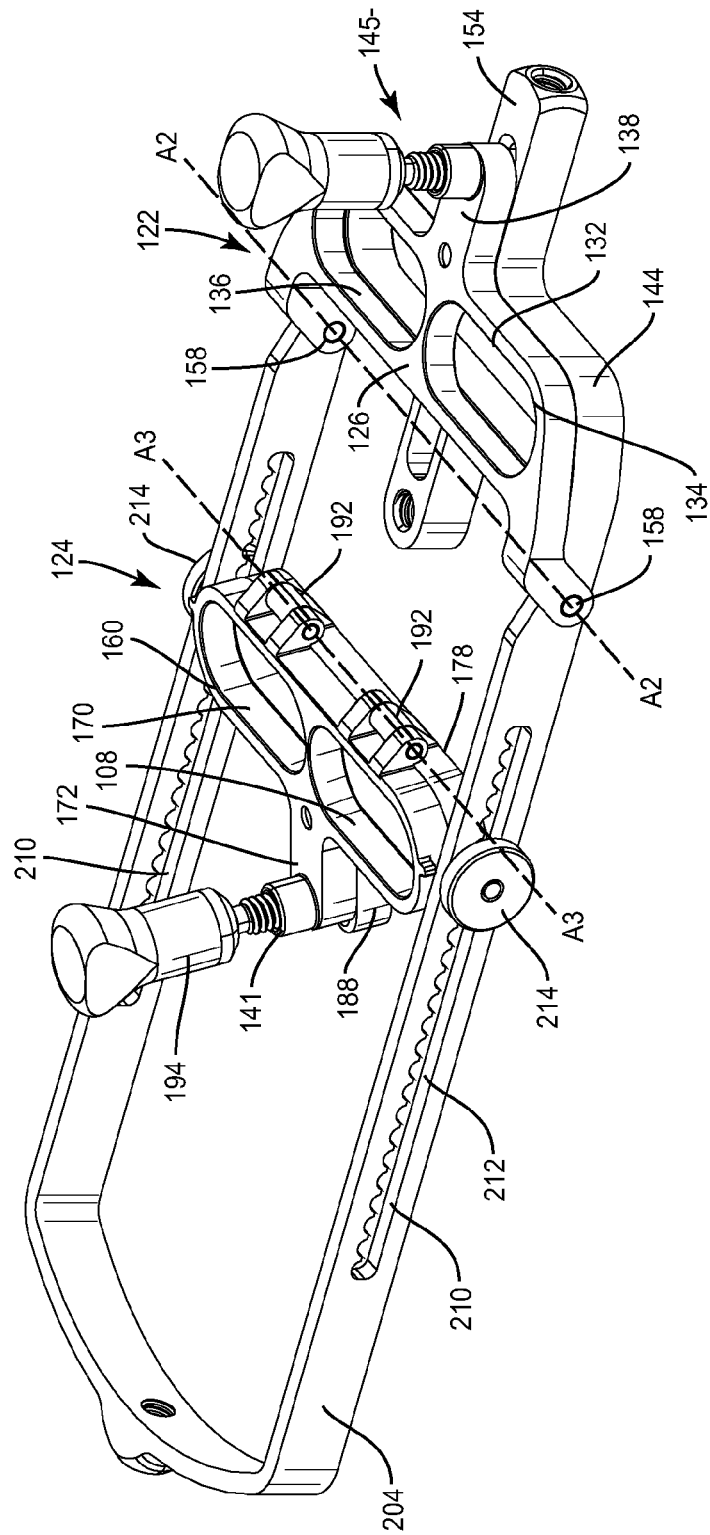
FIG. 10 is a perspective view of components of the system shown in FIG. 9.
Figure 11:
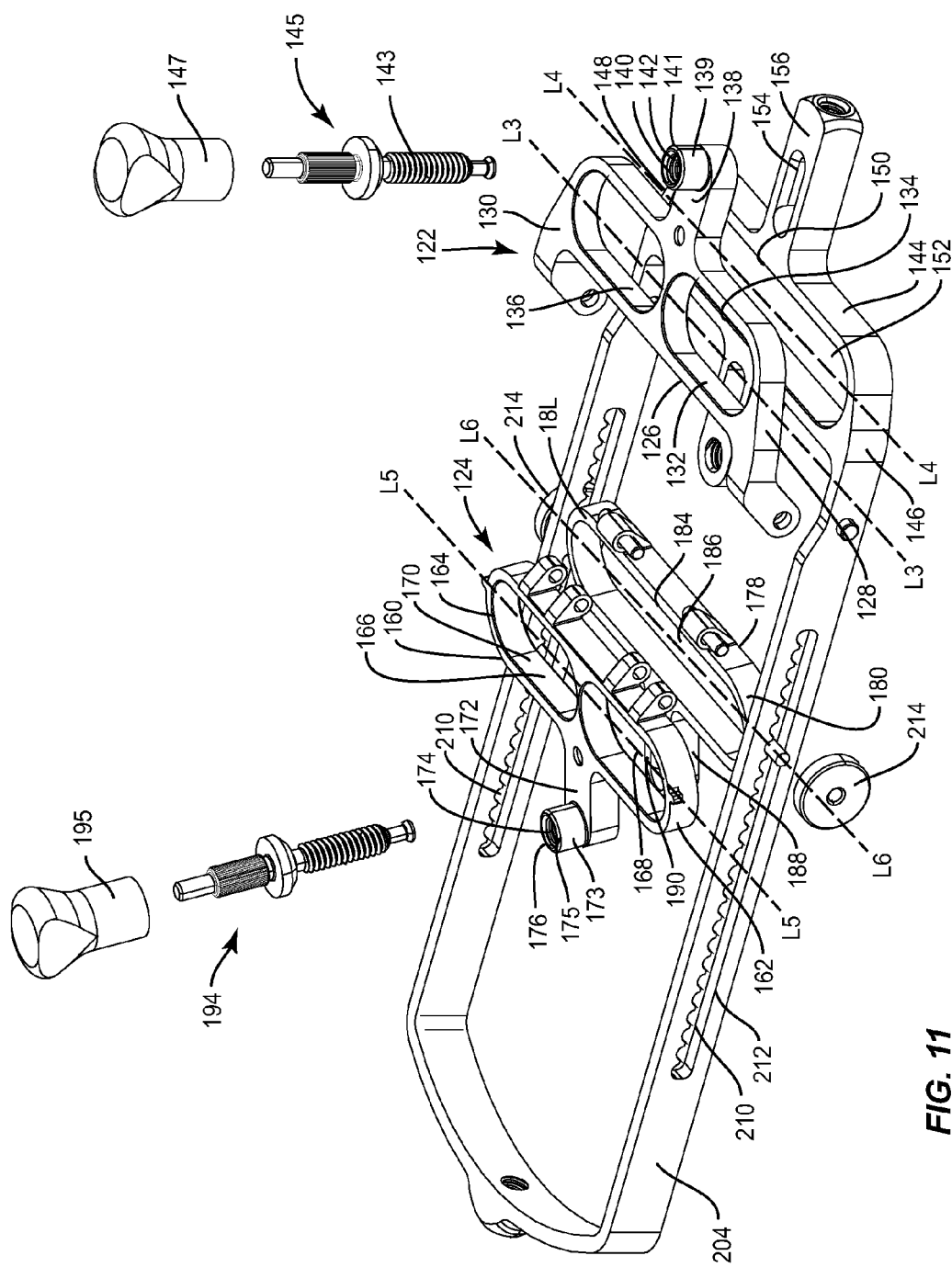
FIG. 11 is a perspective view of the components shown in FIG. 9 with parts separated.

In one embodiment, as shown in FIGS. 9-11, spinal correction system 20, similar to the systems and methods described with regard to FIGS. 1-6, includes a frame 204 comprising a first apparatus 122 and a second apparatus 124. Apparatus 122 includes a first member, such as, for example, a plate 126 defining a longitudinal axis L3. Plate 126 extends between a first end 128 and a second end 130. Plate 126 defines an inner surface 132. Inner surface 132 defines a first cavity, such as, for example, an elongated slot 134 and a second cavity, such as, for example, an elongated slot 136.

Slots 134, 136 are each configured to receive an extender, described below. Slots 134, 136 are spaced apart along axis L3 and disposed in a sagittal plane SP1 of a body in a cephalad-caudal orientation.

Plate 126 includes a flange 138 extending therefrom. Flange 138 includes a cavity, such as, for example, an opening 140. Opening 140 includes an inner surface 142. Inner surface 142 is threaded and opening 140 is configured for disposal of an actuator, discussed herein. Opening 140 includes a raised portion 139 having a face 141 configured for engagement with an actuator, as discussed herein.

Apparatus 122 includes a second member, such as, for example, a plate portion 144 defining a longitudinal axis L4. Plate portion 144 extends between a first end 146 and a second end 148 of frame 204. Plate 144 defines an inner surface 150. Inner surface 150 defines a cavity, such as, for example, an elongated slot 152.

Slot 152 is configured to receive an extender, described herein. Slot 152 extends along axis L4 and is disposed in plane SP1 such that at least a portion of slots 134, 136 and slot 152 are substantially aligned.

Plate 144 includes a flange 154 extending therefrom. Flange 154 includes an engagement surface 156. It is contemplated that surface 156 may have alternate surface configurations, such as, for example, rough, arcuate, undulating, mesh, porous, semi-porous, dimpled and/or textured according to the requirements of a particular application to facilitate engagement with the actuator, as discussed herein.

Plate 126 is connected to plate 144 along an axis A2. Axis A2 is disposed in substantially parallel relation to longitudinal axes L3 and L4. Plates 126, 144 are rotatable about axis A2 between a non-locking configuration and a locking configuration to space apart plates 126, 144 such that inner surfaces 132, 150 forcibly engage the extenders in releasable fixation, as described above. Plates 126, 144 are connected via spaced apart hinges 158 of frame 204. Hinges 158 extend along axis A2 and facilitate relative rotation of plates 126, 144.

A screw jack 145, similar to the component configuration and operation of screw jack 60 described with regard to FIGS. 1-6, is engageable with flanges 138, 154 to drive apart plates 126, 144 and rotate plates 126, 144 about axis A2. A handle 147, similar to the component configuration and actuator operation of handle 64 described with regard to FIGS. 1-6, is mounted with screw jack 145.

Apparatus 124 includes a first member, such as, for example, a plate 160 defining a longitudinal axis L5. Plate 160 extends between a first end 162 and a second end 164. Plate 160 defines an inner surface 166. Inner surface 166 defines a first cavity, such as, for example, a first elongated slot 168 and a second cavity, such as, for example, a second elongated slot 170.

Slots 168, 170 are each configured to receive an extender, described below. Slots 168, 170 are spaced apart along axis L5 and disposed in sagittal plane SP2 of a body in a cephalad-caudal orientation.

Plate 160 includes a flange 172 extending therefrom. Flange 172 includes a cavity, such as, for example, an opening 174. Opening 174 includes an inner surface 176. Inner surface 176 is threaded and opening 174 is configured for disposal of an actuator, discussed herein. Opening 174 includes a raised portion 173 having a face 175 configured for engagement with an actuator, as discussed herein.

Apparatus 124 includes a second member, such as, for example, a plate 178 defining a longitudinal axis L6. Plate 178 extends between a first end 180 and a second end 182. Plate 178 defines an inner surface 184. Inner surface 184 defines a cavity, such as, for example, an elongated slot 186.

Slot 186 is configured to receive an extender, described herein. Slot 186 extends along axis L6 and is disposed in plane SP2 such that at least a portion of slots 168, 170 and slot 186 are substantially aligned.

Plate 178 includes a flange 188 extending therefrom. Flange 188 includes an engagement surface 190. It is contemplated that surface 190 may have alternate surface configurations, such as, for example, rough, arcuate, undulating, mesh, porous, semi-porous, dimpled and/or textured according to the requirements of a particular application to facilitate engagement with the actuator, as discussed herein.

Plate 160 is connected to plate 178 along an axis A3. Axis A3 is disposed in substantially parallel relation to longitudinal axes L5 and L6. Plates 160, 178 are rotatable about axis A3 between a non-locking configuration and a locking configuration to space apart plates 160, 178 such that inner surfaces 166, 184 forcibly engage the extenders in releasable fixation, as described above. Plates 160, 178 are connected via spaced apart hinges 192 along axis A3.

A screw jack 194, similar to the component configuration and operation of screw jack 60 described with regard to FIGS. 1-6, is engageable with flanges 172, 188 to drive apart plates 160, 178 and rotate plates 160, 178 about axis A3. A handle 195, similar to the component configuration and actuator operation of handle 64 described with regard to FIGS. 1-6, is mounted with screw jack 194.

Apparatus 122 and 124 are disposed with frame 204. Frame 204 includes a first end 206 and a second end 208. End 206 is configured to fixedly engage apparatus 122. Second end 208 includes an interior surface 210 that defines elongated slots 212 configured for disposal of apparatus 124. Apparatus 124 is selectively translatable along slots 212 and a transverse plane T1 of a body to selectively orient extenders supported with apparatus 124. As such, the extenders disposed with apparatus 124 are selectively translatable along plane SP2 and plane T1.

Interior surface 210 includes projections 216 that define recesses 218. Upon orientation of the extenders in a selected position, hinges 214 are fixed within a selected recess 218 corresponding to the selected position and orientation. In one embodiment, surface 210 has a scalloped configuration for adjustable and/or selective fixation of hinges 214 along slots 212.

System 20 includes a plurality of extenders 196 and a plurality of extenders 198. Extenders 196 each include an outer surface 200, which are configured for disposal in slots 134, 136 and slot 152 and engagement with the respective inner surfaces. In one embodiment, extenders 196 are configured for disposal with a concave portion of a spine. Extenders 198 each include an outer surface 202, which is configured for disposal in slots 168, 170 and slot 186 and engagement with the respective inner surfaces. In one embodiment, extenders 198 are configured for disposal with a convex portion of a spine.

In assembly, operation and use, apparatus 122 and apparatus 124, similar to the component configuration, methods described and operation of link 57 described with regard to FIGS. 1-6, are each manipulated between a non-locking configuration and a locking configuration to fixedly dispose extenders 196, 198 in a selected position and/or orientation, as described above. Frame 204 includes an axial derotation handle 164 and a lateral derotation handle 165. Forces are applied to handles 164, 165, for example, via manipulation of a practitioner during a surgical treatment, to displace, pull, twist or align vertebrae, according to the requirements of a particular application.

Figure 12:
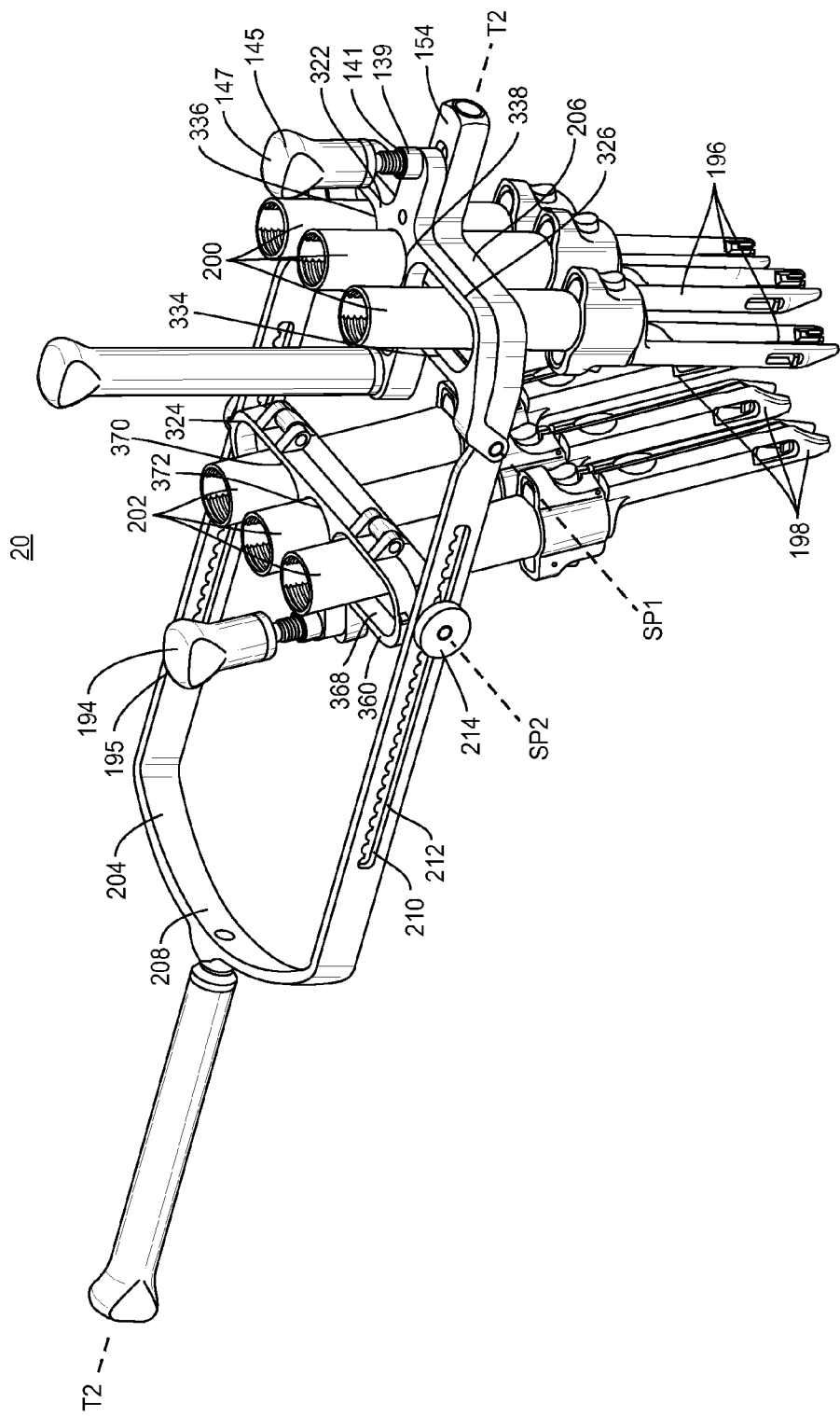
FIG. 12 is a perspective view of one embodiment of a system in accordance with the principles of the present disclosure.
Figure 13:
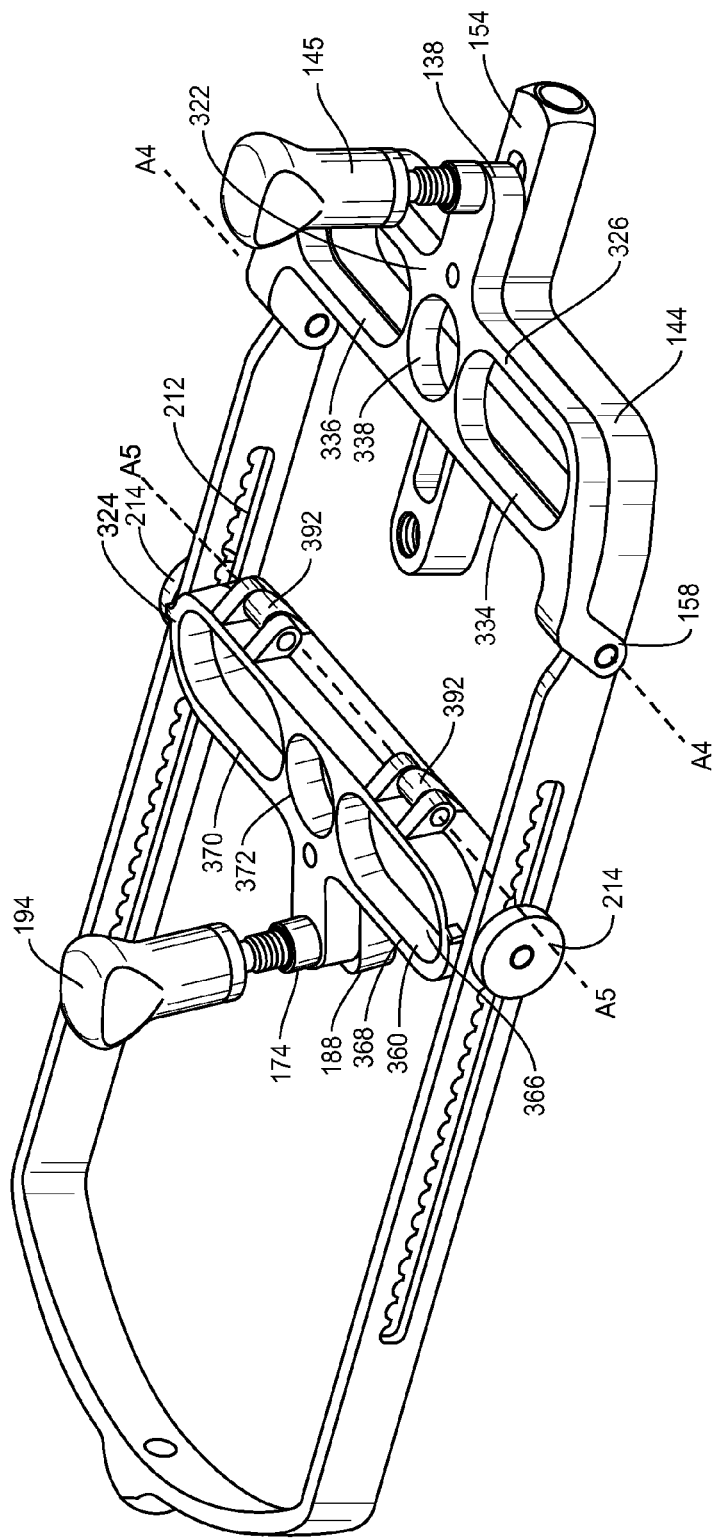
FIG. 13 is a perspective view of components of the system shown in FIG. 12.
Figure 14:
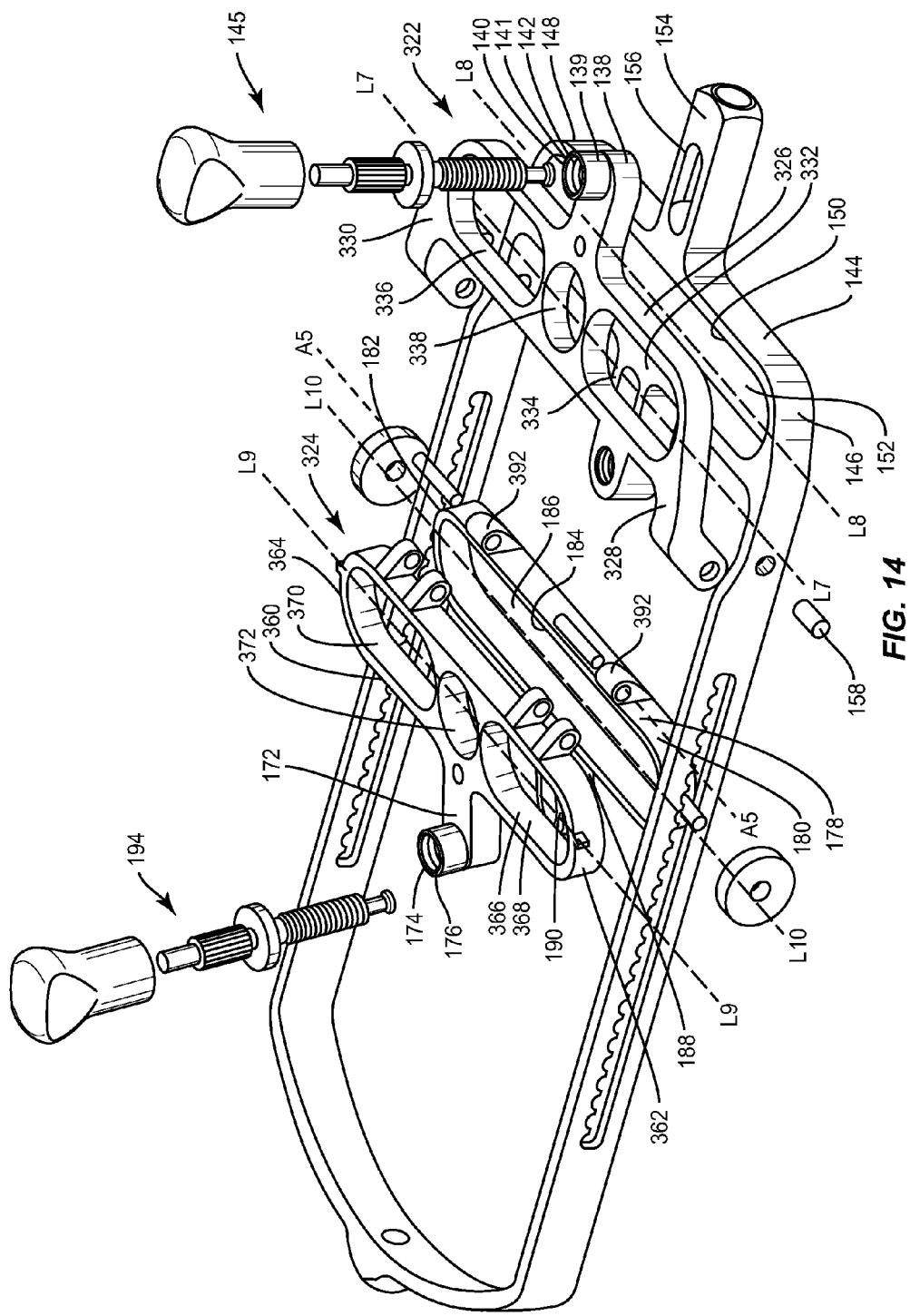
FIG. 14 is a perspective view of the components shown in FIG. 12 with parts separated.

In one embodiment, as shown in FIGS. 12-14, spinal correction system 20, similar to the systems and methods described with regard to FIGS. 9-11, includes frame 204 having an apparatus 322 and an apparatus 324. Apparatus 322 includes a plate 326 defining a longitudinal axis L7. Plate 326 extends between a first end 328 and a second end 330. Plate 326 defines an inner surface 332. Inner surface 332 defines an elongated slot 334, an elongated slot 336 and an opening 338.

Slots 334, 336 and opening 338 are each configured for disposal of an extender. Slots 334, 336 and opening 338 are spaced apart along axis L7 and disposed in a sagittal plane SP1 of a body in a cephalad-caudal orientation.

Plate 326 includes flange 138, described above. Apparatus 322 includes plate portion 144, described above, defining a longitudinal axis L8. Slot 152 extends along axis L8 and is disposed in plane SP1 such that at least a portion of the slots 334, 336 and opening 338, and slot 152 are substantially aligned. Extenders 196 are selectively translatable along plane SP1 within slots 334, 336. In one embodiment, extenders 196 disposed within slots 334, 336 are connected to monoaxial screws. An extender 196 is disposed with opening 338 and fixed relative to plane SP1. In one embodiment, the extender 196 disposed within opening 338 is connected to a MAS.

Plate 326 is connected to plate 144 along an axis A4. Axis A4 is disposed in substantially parallel relation to longitudinal axes L7 and L8. Plates 326, 144 are rotatable about axis A4 between a non-locking configuration and a locking configuration to space apart plates 326, 144 such that inner surfaces 332, 150 forcibly engage the extenders in releasable fixation, as described above. Plates 326, 144 are connected via spaced apart hinges 158 and extend along axis A4.

Screw jack 145, described above, is engageable with flanges 138, 154 to drive apart plates 326, 144 and rotate plates 326, 144 about axis A4. Handle 147, described above, is mounted with screw jack 145.

Apparatus 324 includes a plate 360 defining a longitudinal axis L9. Plate 360 extends between a first end 362 and a second end 364. Plate 360 defines an inner surface 366. Inner surface 366 defines an elongated slot 368, an elongated slot 370 and an opening 372.

Slots 368, 370 and opening 372 are each configured for disposal of an extender. Slots 368, 370 and opening 372 are spaced apart along axis L9 and disposed in sagittal plane SP2 in a cephalad-caudal orientation.

Plate 360 includes a flange 172, described above. Apparatus 324 includes plate 178, described above, defining a longitudinal axis L10. Slot 186 extends along axis L10 and is disposed in plane SP2 such that at least a portion of slots 368, 370 and opening 372 and slot 186 are substantially aligned. Extenders 198 are selectively translatable along plane SP2 within slots 368, 370. In one embodiment, extenders 198 disposed within slots 368, 370 are connected to mono-axial screws. An extender 198 is disposed with opening 372 and fixed relative to plane SP2. In one embodiment, the extender 198 disposed within opening 372 is connected to a MAS.

Plate 360 is connected to plate 178 along an axis A5. Axis A5 is disposed in substantially parallel relation to longitudinal axes L9 and L10. Plates 360, 178 are rotatable about axis A5 between a non-locking configuration and a locking configuration to space apart plates 360, 178 such that inner surfaces 366, 184 forcibly engage the extenders in releasable fixation, as described above. Plates 360, 178 are connected via spaced apart hinges 392 and extend along axis A5.

Screw jack 194, described above, is engageable with flanges 172, 188 to drive apart plates 360, 178 and rotate plates 360, 178 about axis A5. Handle 195, described above, is mounted with screw jack 194.

Figure 15:
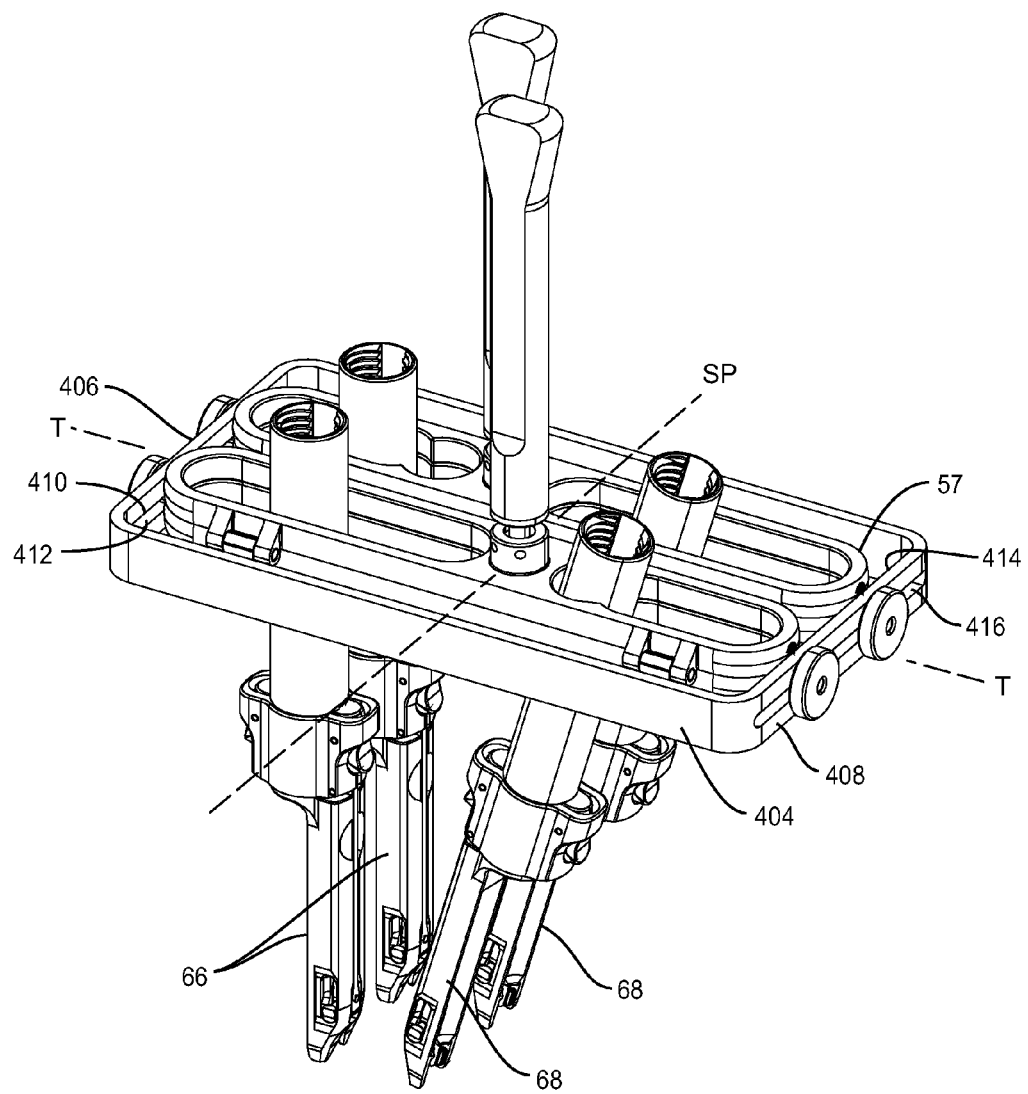
FIG. 15 is a perspective view of one embodiment of a system in accordance with the principles of the present disclosure.
Figure 16:
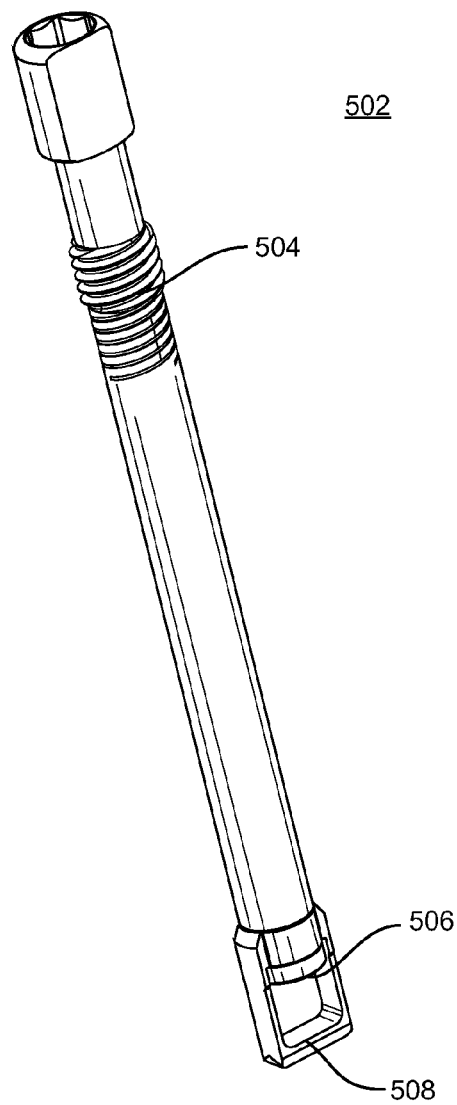
FIG. 16 is a perspective view of a component of one embodiment of a system in accordance with the principles of the present disclosure.
Figure 17:
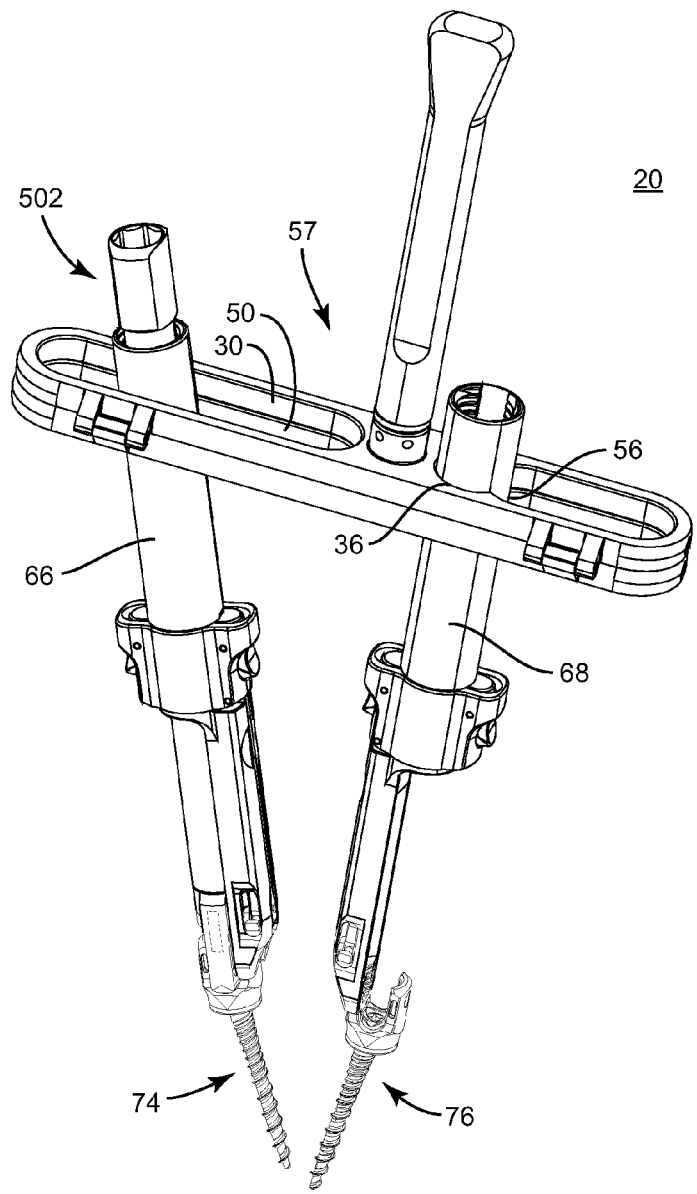
FIG. 17 is a perspective view of one embodiment of a system in accordance with the principles of the present disclosure.
Figure 18:
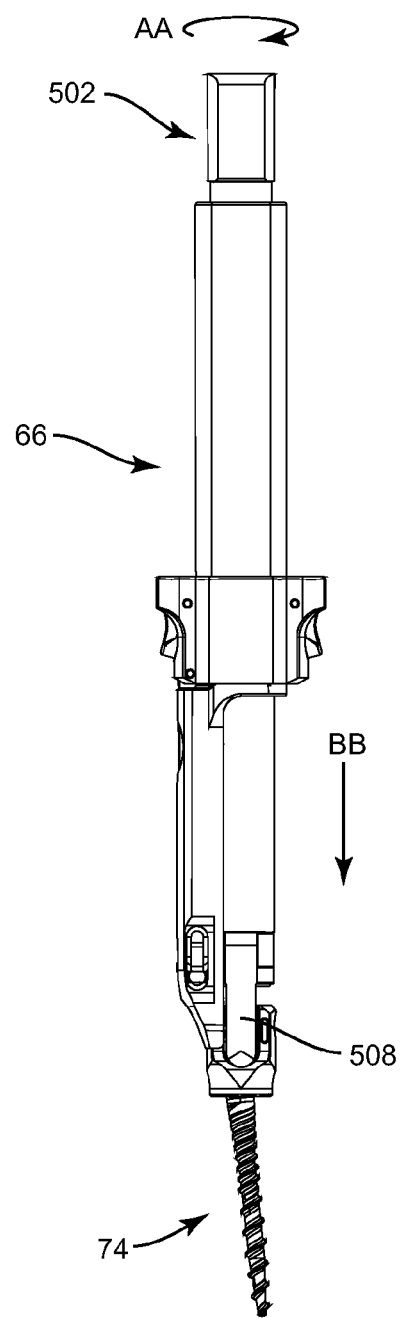
FIG. 18 is a perspective view of components of the system shown in FIG. 17.

In one embodiment, as shown in FIG. 15, spinal correction system 20, similar to the systems and methods described with regard to FIGS. 1-6, includes a frame 404 comprising segmental links 57, described above. It is envisioned that frame 404 can include one or a plurality of links 57. Extenders 66, 68 are disposed with links 57 for relative translation and releasable fixation, as described above. Links 57 are disposable between a non-locking configuration and a locking configuration to forcibly engage extenders 66, 68 in releasable fixation, as described above.

Frame 404 includes a first end 406 and a second end 408. Ends 406, 408 are configured to support links 57 via hinges, similar to those described herein, for slidable movement relative thereto along a sagittal plane SP in a cephalad-caudal orientation. End 406 includes an interior surface 410 that defines an elongated slot 412 configured for disposal of one end of links 57. End 408 includes an interior surface 414 that defines an elongated slot 416 configured for disposal of the other end of links 57. Links 57 are selectively translatable along slots 412, 416 in a sagittal plane SP a body to selectively orient extenders 66, 68. As such, extenders 66, 68 disposed with links 57 are selectively translatable along plane SP and plane T.

In one embodiment, as shown in FIGS. 16-20, spinal correction system 20, similar to the systems and methods described with regard to FIGS. 1-6, includes segmental link 57, described above, and a screw locker instrument 502 configured for disposal with extender 66 and a MAS 74. Instrument 502 is engageable with MAS 74 to facilitate locking of the linkage of system 20.

Figure 20:
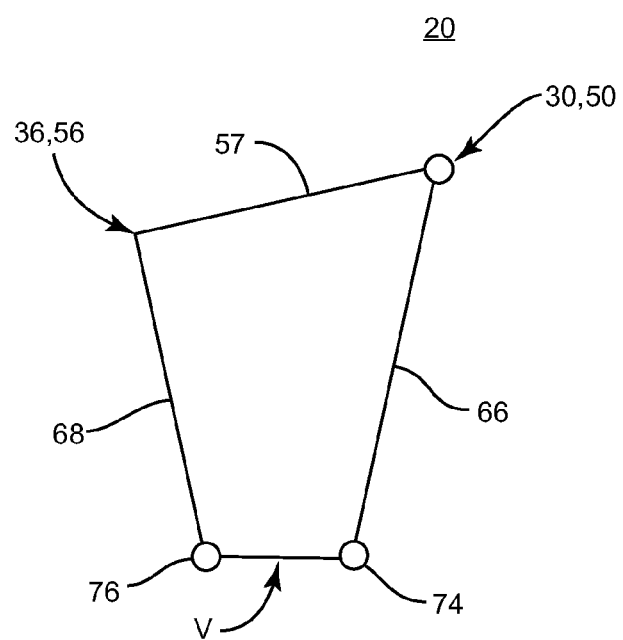
FIG. 20 is a schematic representation of one embodiment of a system in accordance with the principles of the present disclosure disposed with vertebrae.

Link 57 is configured with a linkage of system 20 employed with a MAS 74 and a MAS 76. The linkage of system 20 includes a first joint, such as, for example, extender 66 disposed with slots 30, 50 described above, a second joint, such as, for example, the spherical joint of the MAS crown and the MAS bone screw of MAS 74 and a third joint, such as, for example, the spherical joint of the MAS crown and the MAS bone screw of MAS 76, as shown in FIG. 20. Extender 68 is disposed with portions 36, 56 described above, such that link 57 is disposed perpendicular to extender 68 and the connection of link 57 with extender 68 is fixed.

Figure 19:
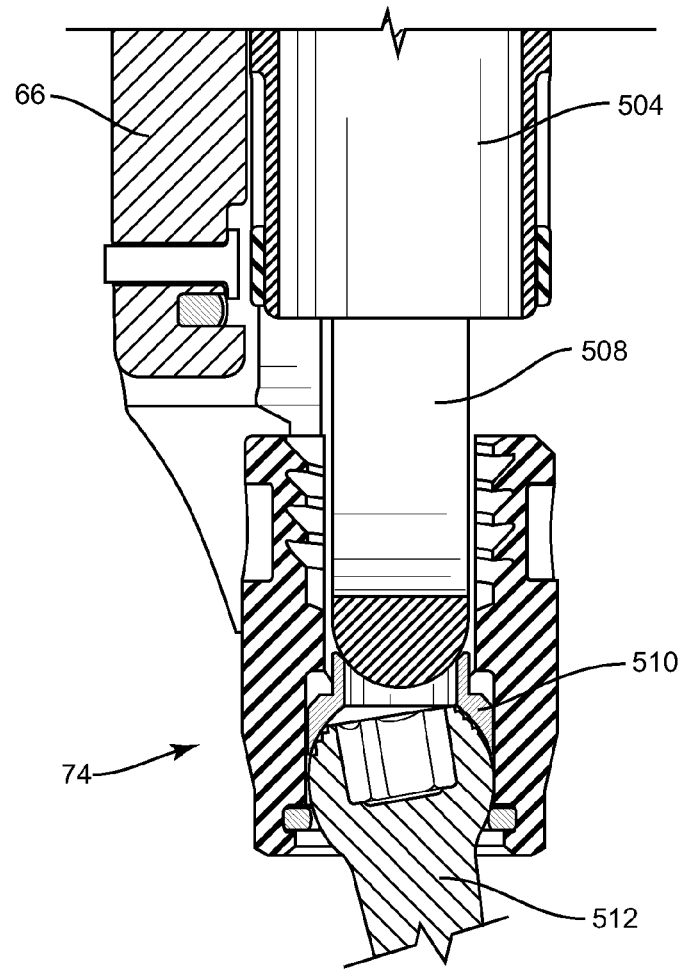
FIG. 19 is a break away cross section view of components of the system shown in FIG. 17.

Instrument 502 includes a threaded shaft 504 and a retaining ring 506 configured for releasable fixation with extender 66. Shaft 504 is rotatable for threaded engagement with an interior threaded surface of extender 66 to cause axial translation of shaft 504 relative to extender 66. As shaft 504 is rotated, in the direction shown by arrow AA in FIG. 18, shaft 504 is caused to translate axially, in the direction shown by arrow BB. Shaft 504 includes an engagement member 508 that applies a force to the spherical joint of MAS 74, which includes MAS crown 510 and MAS bone screw 512, as shown in FIG. 19. Engagement of member 508 with crown 510 and screw 512 causes the spherical joint of MAS 74 to become fixed and lock in a selected orientation such that the first and third joints facilitate fixing link 57 in the locking configuration, as described herein.

Figure 21:
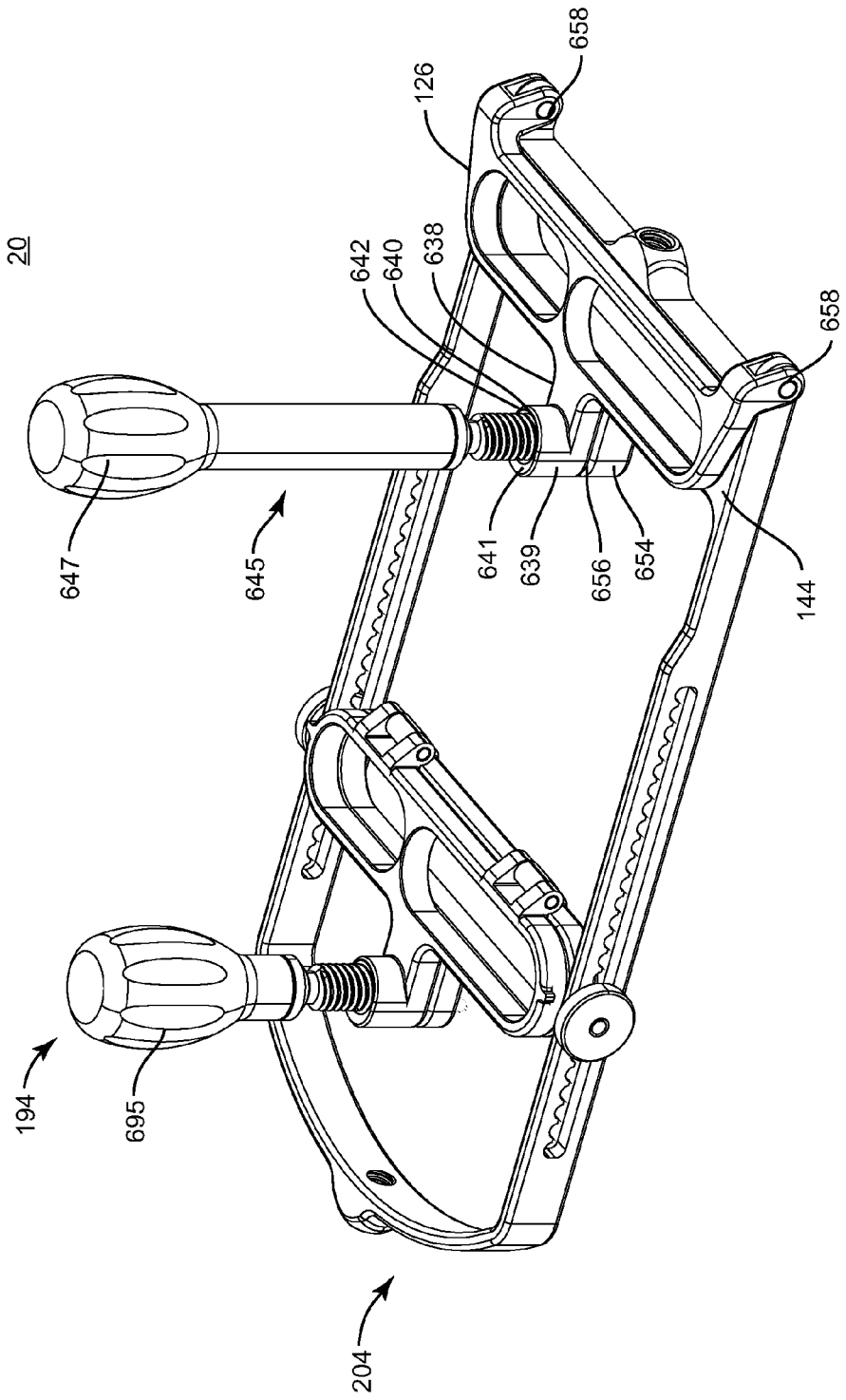
FIG. 21 is a perspective view of one embodiment of a system in accordance with the principles of the present disclosure.

In one embodiment, as shown in FIG. 21, spinal correction system 20, similar to the systems and methods described with regard to FIGS. 9-11, includes frame 204 described above. Plate 126, described above, includes a flange 638 extending therefrom. Flange 638 includes an opening 640. Opening 640 includes an inner surface 642. Inner surface 642 is threaded and opening 640 is configured for disposal of an actuator, discussed herein. Opening 640 includes a raised portion 639 having a face 641 configured for engagement with an actuator, as discussed herein.

Plate 144, described above, includes a flange 654 extending therefrom. Flange 654 includes an engagement surface 656. Plates 126, 144 are connected via spaced apart hinges 658 disposed with a concave side end of frame 204.

A screw jack 645, similar to the component configuration and operation of screw jack 145 described with regard to FIGS. 9-11, is engageable with flanges 638, 654 to drive apart plates 126, 144 and rotate plates 126, 144, as described above. An ellipsoid shaped, dorsal handle 647, similar to the component configuration and operation of handle 64 described with regard to FIGS. 1-6, is permanently mounted with screw jack 645. Handle 647 includes gripping elements disposed circumferentially thereabout. In one embodiment, handle 647 is employed to apply a derotation force to implant holders, as described herein.

Screw jack 194, described above, includes an ellipsoid shaped, dorsal handle 695, similar to the component configuration and operation of handle 64 described with regard to FIGS. 1-6, which is permanently mounted with screw jack 194. Handle 695 includes gripping elements disposed circumferentially thereabout.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal correction system comprising:
  a first apparatus comprising a first member defining a longitudinal axis and including a first end comprising a first inner surface that defines a first cavity and a second end comprising a second inner surface that defines a second cavity, the first end being fixed relative to the second end, and a second member defining a longitudinal axis and including a first end comprising a first inner surface that defines a first cavity and a second end comprising a second inner surface that defines a second cavity, the members being connected along a first axis disposed in substantially parallel relation to the longitudinal axes such that the first cavities are substantially aligned and the second cavities are substantially aligned;

a second apparatus comprising a first member defining a longitudinal axis and including a first end comprising a first inner surface that defines a first cavity and a second end comprising a second inner surface that defines a second cavity, and a second member defining a longitudinal axis and including a first end comprising a first inner surface that defines a first cavity and a second end comprising a second inner surface that defines a second cavity, the members of the second apparatus being connected along a second axis disposed in substantially parallel relation to the longitudinal axes of the members of the second apparatus;

a frame configured for disposal of the first and second apparatuses;

a plurality of concave implant supports, each concave implant support configured for disposal within a respective cavity of the first apparatus; and a plurality of convex implant supports, each convex implant support configured for disposal within a respective cavity of the second apparatus, wherein the members of the first apparatus are rotatable about the first axis to space apart the members of the first apparatus such that the inner surfaces forcibly engage the concave implant supports in releasable fixation and the members of the second apparatus are rotatable about the second axis to space apart the members of the second apparatus such that the inner surfaces forcibly engage the convex implant supports in releasable fixation.

2. The system as recited in claim 1, wherein the supports define a transverse plane such that the members are rotatable relative to the transverse plane.

3. The system as recited in claim 1, wherein the members of the first apparatus are rotatable between a first configuration such that the members of the first apparatus are translatable longitudinally along the concave implant supports and a second configuration such that the inner surfaces of the first apparatus forcibly engage the concave implant supports in releasable fixation to prevent longitudinal translation of the members of the first apparatus along the concave implant supports.

4. The system as recited in claim 1, wherein the members of the first apparatus are rotatable between a first configuration such that the concave implant supports are translatable along the first axis within the respective cavities of the first apparatus and a second configuration such that the inner surfaces of the first apparatus forcibly engage the concave implant supports in releasable fixation.

5. The system as recited in claim 1, wherein each of the first cavities includes an elongated slot and each of the second cavities includes an elongated slot.

6. The system as recited in claim 5, wherein at least a portion of the slots of the first cavities of the first apparatus are disposed in substantial alignment and at least a portion of the slots of the second cavities of the first apparatus are disposed in substantial alignment.

7. The system as recited in claim 1, wherein each of the first cavities of the first apparatus includes a slot having an elongated portion configured for disposal of a support along the first axis and an arcuate portion configured to prevent translation of a support along the first axis.

8. The system as recited in claim 1, wherein the first cavities of the first apparatus are aligned with the second cavities of the first apparatus in a cephalad-caudal orientation such that the respective concave implant supports are translatable in a sagittal plane.

9. The system as recited in claim 1, wherein the members of the first apparatus are connected via at least one hinge that defines the first axis.

10. The system as recited in claim 1, wherein the members of the first apparatus are connected via a first hinge and a second hinge spaced apart from the first hinge, the hinges defining the first axis.

11. The system as recited in claim 1, further comprising an actuator engageable with the members of the first apparatus in a configuration to rotate the members of the first apparatus about the first axis and space apart the members of the first apparatus.

12. The system as recited in claim 11, wherein the actuator translates relative to the first member of the first apparatus to engage the second member of the first apparatus and space apart the members of the first apparatus.

13. The system as recited in claim 11, wherein the actuator includes a screw jack threaded with and translatable relative to the first member of the first apparatus for engagement with the second member of the first apparatus to space apart the members of the first apparatus.

14. The system as recited in claim 11, wherein the actuator includes a spring.

15. The system as recited in claim 11, wherein the actuator includes a handle attached with the members of the first apparatus and being configured to facilitate derotation of vertebrae.

16. The system as recited in claim 1, further comprising an instrument disposed within the first cavities of the first apparatus and being movable relative to the concave implant supports in a configuration to fix a bone fastener connected with one of the concave implant supports in a selected orientation.

17. The system as recited in claim 1, wherein the first and second cavities of the first member of the first apparatus are spaced apart and disposed in a first sagittal plane, and the first and second cavities of the second member of the first apparatus are spaced apart from one another and disposed in the first sagittal plane.

18. The system as recited in claim 17, wherein the first and second cavities of the first member of the second apparatus are spaced apart from one another and disposed in a second sagittal plane, and the first and second cavities of the second member of the second apparatus are spaced apart from one another and disposed in the second sagittal plane.

19. A spinal correction system comprising:

a first apparatus comprising a first plate extending between a first end and a second end and defining a longitudinal axis, the first end including a first inner surface that defines a first elongated slot and the second end including a second inner surface that defines a second elongated slot, the slots being spaced apart and configured to be disposed in a transverse plane of a body, the first end being fixed relative to the second end and a second plate extending between a first end and a second end and defining a longitudinal axis, the first end of the second plate including a first inner surface that defines a first elongated slot and the second end of the second plate including a second inner surface that defines a second elongated slot, the slots of the second plate being spaced apart and configured to be disposed in the transverse plane such that at least a portion of the first slots are substantially aligned and at least a portion of the second slots are substantially aligned, the plates being connected along a first axis disposed in substantially parallel relation to the longitudinal axes;

a second apparatus comprising a first plate extending between a first end and a second end and defining a longitudinal axis, the first end of the first plate of the second apparatus including a first inner surface that defines a first elongated slot and the second end of the first plate of the second apparatus including a second inner surface that defines a second elongated slot, the slots of the first plate of the second apparatus being spaced apart and configured to be disposed in the transverse plane of a body, and a second plate extending between a first end and a second end and defining a longitudinal axis, the first end of the second plate of the second apparatus including a first inner surface that defines a first elongated slot and the second end of the second plate of the second apparatus including a second inner surface that defines a second elongated slot, the slots of the second plate of the second apparatus being spaced apart and configured to be disposed in the transverse plane such that at least a portion of the first slots of the second apparatus are substantially aligned and at least a portion of the second slots of the second apparatus are substantially aligned, the plates of the second apparatus being connected along a second axis disposed in substantially parallel relation to the longitudinal axes of the second apparatus;

a frame configured for disposal of the first and second apparatuses;

a plurality of concave extenders, each concave extender configured for disposal within a respective slot of the first apparatus; and a plurality of convex extenders, each convex extender configured for disposal within a respective slot of the first apparatus, wherein the plates of the first apparatus are rotatable about the first axis between a non-locking configuration and a locking configuration such that the plates of the first apparatus are spaced apart and the inner surfaces of the first apparatus forcibly engage the concave extenders in releasable fixation and the plates of the second apparatus are rotatable about the second axis between a non-locking configuration and a locking configuration such that the plates of the second apparatus are spaced apart and the inner surfaces of the second apparatus forcibly engage the convex extenders in releasable fixation.

20. A spinal correction system comprising:

a frame configured for disposal of a first apparatus and a second apparatus, the first apparatus including a first member defining a longitudinal axis and including a first end comprising a first inner surface that defines a first cavity and a second end comprising a second inner surface that defines a second cavity, the first and second cavities being disposed in a first sagittal plane and spaced apart from one another, and a second member defining a longitudinal axis and including a first end comprising a first inner surface that defines a first cavity and a second end comprising a second inner surface that defines a second cavity, the first and second cavities of the second member being disposed in the first sagittal plane and spaced apart from one another, the members being connected along a first axis disposed in substantially parallel relation to the longitudinal axes such that the first cavities are substantially aligned and the second cavities are substantially aligned, the second apparatus including a first member defining a longitudinal axis and including a first end comprising a first inner surface that defines a first cavity and a second inner surface that defines a second cavity, the first and second cavities of the first member of the second apparatus being disposed in a second sagittal plane and spaced apart from one another, and a second member defining a longitudinal axis and including a first inner surface that defines a first cavity and a second inner surface that defines a second cavity, the first and second cavities of the second member of the second apparatus being disposed in the second sagittal plane and spaced apart from one another, the members of the second apparatus being connected along a second axis disposed in substantially parallel relation to the longitudinal axes of the members of the second apparatus;

a plurality of concave extenders, each concave extender configured for disposal within a respective cavity of the first apparatus; and a plurality of convex extenders, each convex extender configured for disposal within a respective cavity of the second apparatus, wherein the members of the first apparatus are rotatable about the first axis to space apart the members of the first apparatus such that the inner surfaces forcibly engage the concave extenders in releasable fixation and the members of the second apparatus are rotatable about the second axis to space apart the members of the second apparatus such that the inner surfaces forcibly engage the convex extenders in releasable fixation.

* * * * *

UNITED STATES PATENT AND TRADEMARK OFFICE
CERTIFICATE OF CORRECTION

| | | |
|---|---|---|
| PATENT NO. | : 9,155,573 B2 | Page 1 of 1 |
| APPLICATION NO. | : 13/659590 | |
| DATED | : October 13, 2015 | |
| INVENTOR(S) | : May et al. | |

It is certified that error appears in the above-identified patent and that said Letters Patent is hereby corrected as shown below:

In the Specification

In Column 7, Line 37, delete "plates 28, 48" and insert -- plates 22, 42 --, therefor.

In Column 7, Line 48, delete "screw jack 62" and insert -- screw jack 60 --, therefor.

Signed and Sealed this
Tenth Day of May, 2016

Michelle K. Lee
*Director of the United States Patent and Trademark Office*